United States Patent
Singh et al.

(10) Patent No.: US 8,605,858 B2
(45) Date of Patent: Dec. 10, 2013

(54) METHODS AND SYSTEMS FOR INSPECTING STRUCTURES FOR CRYSTALLOGRAPHIC IMPERFECTIONS

(75) Inventors: Surendra Singh, Chandler, AZ (US); Andy Szuromi, Phoenix, AZ (US); Vladimir K. Tolpygo, Scottsdale, AZ (US); Andy Kinney, Chandler, AZ (US)

(73) Assignee: Honeywell International Inc., Morristown, NJ (US)

( * ) Notice: Subject to any disclaimer, the term of this patent is extended or adjusted under 35 U.S.C. 154(b) by 346 days.

(21) Appl. No.: 13/169,902

(22) Filed: Jun. 27, 2011

(65) Prior Publication Data

US 2012/0328079 A1     Dec. 27, 2012

(51) Int. Cl.
*G01N 23/207* (2006.01)

(52) U.S. Cl.
USPC .............................................. 378/73; 378/71

(58) Field of Classification Search
USPC ....................................................... 378/70–90
See application file for complete search history.

(56) References Cited

U.S. PATENT DOCUMENTS

| | | |
|---|---|---|
| 4,696,024 A | 9/1987 | Pesch |
| 5,136,624 A | 8/1992 | Schnieder et al. |
| 5,193,104 A | 3/1993 | Bastie et al. |
| 5,588,034 A | 12/1996 | Bowen et al. |
| 6,198,796 B1 | 3/2001 | Yokoyama et al. |
| 6,775,350 B2 | 8/2004 | Emons et al. |
| 6,907,107 B1 | 6/2005 | Wallis et al. |
| 7,158,609 B2 | 1/2007 | Kikuchi et al. |
| 2008/0159479 A1 | 7/2008 | Huang et al. |
| 2010/0027746 A1 | 2/2010 | Park et al. |
| 2011/0038457 A1 | 2/2011 | Huang et al. |

*Primary Examiner* — Courtney Thomas
(74) *Attorney, Agent, or Firm* — Ingrassia Fisher & Lorenz, P.C.

(57) ABSTRACT

Embodiments of methods and systems for inspecting a structure for a crystallographic imperfection are provided. In the method, an X-ray wavelength that is particularly susceptible to diffraction by the crystallographic imperfection is identified. Then an X-ray source is provided to emit X-rays in the identified X-ray wavelength. While placing the structure at a sequence of positions relative to the X-ray source, X-rays are directed at the structure in multiple, non-parallel arrays to create sequential patterns of diffracted X-rays. The patterns of diffracted X-rays are digitally captured and communicated to a computer that compares them to locate the crystallographic imperfection. For a surface imperfection, the imperfection may be marked with a target to allow for physical removal.

20 Claims, 4 Drawing Sheets

METHODS AND SYSTEMS FOR INSPECTING STRUCTURES FOR CRYSTALLOGRAPHIC IMPERFECTIONS

FIELD OF THE INVENTION

The present invention relates generally to methods and systems for inspecting materials possessing a crystallographic structure, and more particularly relates to methods and systems for locating crystallographic imperfections in materials with crystallographic structures.

BACKGROUND OF THE INVENTION

Currently, superalloys are widely used for applications in which high stresses must be endured at elevated temperatures, for instance in the components of gas turbine engines, such as blades and vanes. Improvements in manufacturing methods have led to casting of components in single-crystal form, resulting in improved high-temperature lives and strength over conventionally prepared metallic materials that included a plurality of grains separated by grain boundaries.

Due to the improved performance of single-crystal superalloy components, the ability to withstand severe operating conditions is expected. However, one or more significant departures from single-crystal perfection may seriously limit the ability of a single-crystal superalloy component to perform under severe operating conditions, and may shorten the service life of the component. Because, the likelihood of fracture and separation along crystallographic boundaries around imperfections is increased, castings for turbine blades and vanes require close inspection for spurious grains and other crystallographic imperfections. The current industry practice is to use an etching process to reveal the spurious grains and crystallographic imperfections on the surface of single-crystal castings. After etching, the casting is visually inspected to evaluate the etched surface relative to the appropriate acceptance criteria for the intended use of the casting.

While etching processes have historically provided good grain contrast for revealing the external grain structure of equiaxed and polycrystalline directionally solidified superalloy castings, these etching processes tend to be inspector dependant, are time-consuming, and may result in dimensional nonconformance due to excessive stock loss, especially given the relatively thin walls of internally cooled components. Stock loss can be very significant if the overall etching process has to be repeated due to insufficient 'readability' of grain. Further, the etching processes may suffer issues with the presence of scale, with a lack of reflectivity, or with various confounding or masking effects such as anodizing iridescence (aka bluing), which may result in failure to reveal, identify, or locate imperfections, or in difficulty in revealing, identifying or locating imperfections.

Accordingly, it is desirable to provide methods and systems for inspecting single-crystal superalloy castings without etching. Also, it is desirable to provide methods and systems for inspecting single-crystal superalloy castings that use X-ray diffraction (XRD) to locate surface and subsurface imperfections. Furthermore, other desirable features and characteristics of the present invention will become apparent from the subsequent detailed description of the invention and the appended claims, when taken in conjunction with the accompanying drawings and this background of the invention.

SUMMARY OF THE INVENTION

Methods and systems for inspecting castings are provided herein. The methods and systems may be used to inspect or characterize the external and internal grain structure of any material possessing a crystallographic structure in which satisfying the Bragg angle geometry would cause X-rays of suitable wavelengths to be diffracted. Such materials include conventional (i.e., equiaxed) castings, polycrystalline directionally solidified (i.e., DS) castings, single-crystal superalloy castings, wrought material (e.g., duplex or large grain in forgings, excessive grain growth resulting from improper cold work and/or heat treatment) and crystalline non-metallic materials.

The methods and systems reverse an important signal-to-noise relationship in conventional radiographic inspection technology. Namely, the ratio of the desired effect of relative X-ray absorption (density/thickness of sound metal versus density/thickness of discontinuities) compared to an undesirable effect called 'grain diffraction' (i.e., mottling). Mottling of an X-ray image appears as blotches corresponding to where certain grains have diverted (by diffraction) the otherwise straight-line path of the local X-ray beam.

A grain which diverts a significant portion of the X-ray beam will tend to appear on film (or sensor image) as having a higher density (as if the diverted beam was absorbed). If the diverted X-rays happen to be superimposed on an area of sound metal, that area or blotch (receiving extra X-rays) will appear to have a lower density, which is similar in appearance to porosity. This phenomenon results in false positives for shrinkage porosity and requires great effort in conventional radiography to minimize XRD.

In other words, the method and system herein optimize the otherwise undesirable X-ray diffraction effect, yet may retain some aspects of a conventional X-ray image of the casting to serve as a reference to assist in locating the crystallographic imperfection on a particular casting. In some instances, the method and system can sufficiently detect some of the larger size conventional discontinuities (e.g. porosity, inclusions, separations, etc.) to serve as an early screening inspection for such conditions.

Because mottling can masquerade as porosity or otherwise interfere with proper interpretation of an X-ray image, industrial X-ray machines considered for foundry uses have special wavelength filters or are operated at voltages or with special X-ray emitting tubes to reduce mottling.

Unlike other methods that utilize X-ray diffraction and require highly-collimated, narrowly-focused X-ray beams or highly-parallel X-ray beams, the method and system herein do not. In fact, the present method ands system utilize X-rays that fan out from the X-ray source in multiple, non-parallel arrays to enable multiple opportunities to satisfy Bragg angle conditions, thus achieving efficient inspection of very large castings or possibly multiple castings.

While the analogy to conventional X-ray may suggest that only the transmission mode of capturing XRD information is used, it is envisioned that the back-reflection mode may also provide vital complementary data.

In accordance with an exemplary embodiment, a method for inspecting a single-crystal superalloy casting comprises the initial step of identifying an X-ray wavelength susceptible to diffraction by a crystallographic imperfection. During this step, an X-ray wavelength that exhibits significant diffraction upon encountering a crystallographic imperfection in a casting is identified. The diffraction of X-rays of specific wavelength by satisfying the Bragg angle crystallographic geometry is well known in the industry and needs no further discussion beyond awareness of those X-ray wavelengths likely to be most useful. The Laue method, which may either be back-reflection mode or transmission mode enables measurement of the specific crystallographic nature of the detected grain imperfection. While use of a monochromatic X-ray may result from the identification of the X-ray wavelength, it is also envisioned that the identified wavelength may include a defined band of X-ray wavelength, or even a plurality of non-continuous bands of X-ray wavelengths. Further, distinct bands of X-ray frequencies may be identified, with each band exhibiting significant diffraction for a different type of crystallographic imperfection. The use of multiple x-ray wavelengths may shorten the inspection time or provide a diagnostic tool by which certain crystallographic imperfections may be better characterized.

In order to maximize diffraction by the crystallographic imperfection during inspection, the method further provides for limiting or tuning the X-ray source so that it emits beams of X-rays within the identified wavelength or beams having a high fraction of X-rays within the identified wavelength. Further, the X-ray source may be enhanced so that it emits an enhanced beam having a selected profile of X-rays in the identified X-ray wavelength, such as a selected percentage of X-rays at one wavelength and a selected percentage of X-rays at another wavelength or multiple wavelengths.

After the X-ray wavelength is identified and the X-ray source readied to produce the desired beam, a casting to be inspected is placed at an initial position relative to the X-ray source. The relative position of the casting includes both its relative location in the x-, y-, and z-directions and its relative orientation about the x-, y-, and z-axes. Typically, the casting is placed on a mount or nest that may be automatically moved to the initial position by a computer. More than one casting may be simultaneously inspected depending on creation of a suitable multi-nest design.

For inspection, the X-ray source directs a divergent beam or stream of X-rays in the identified X-ray wavelengths at the casting for a selected exposure time for diffraction by any crystallographic imperfection therein to create a pattern of diffracted X-rays. For those rays passing through the casting (i.e., transmission X-rays), the pattern of diffracted X-rays is created behind the casting (relative to the X-ray source). For the rays diffracted back from the casting (i.e., back-reflected X-rays), the pattern of diffracted X-rays is created before the casting (again, relative to the X-ray source).

For either or both transmission and back-reflected X-rays, the pattern of diffracted X-rays is captured by a digital image capture device. As is understood, a capture device capable of detecting or sensing relevant X-rays to sufficient resolution is positioned behind the casting for transmission X-rays, and a capture device is positioned between the X-ray source and the casting for back-reflected X-rays.

After the pattern of diffracted X-rays is captured, the capture device communicates the pattern to a computer. Then the computer causes the casting to be placed at a second position and the X-ray source directs a beam at the casting to create a second pattern of diffracted X-rays. The repositioning may involve 'centering' or lateral movement of part relative to the X-ray beam or may involve tilting the part in one or more planes. This process is repeated for sequential positions for a predetermined number of patterns or until the computer determines that an adequate number of patterns has been captured for analysis. During or after the sequential capture of patterns, the computer compares the patterns to locate any crystallographic imperfections on or within the casting. Further, the computer may identify a volume on or in the casting with possible imperfections and may thereafter control placement of the casting to focus on that volume for further inspection.

For purposes of correction, rework, or investigation, the method can include marking the detected crystallographic imperfection with a target such as a dab of paint or outlining circle, oval, etc. For instance, a relatively superficial imperfection on the surface of a casting may be physically removed to allow use of the casting. Therefore, marking the imperfection with the target allows for a removal operator to visually observe where the imperfection is before and during the removal process. For subsurface imperfections, a surface target also may be used, along with printed depth, periphery, or location information. The use of X-ray Computed Aided Tomography is well known method for three-dimensional mapping of internal imperfections and would be applicable for this method as well. In addition or in the alternative to marking, the method can provide for creation of a map of the casting including the location and three-dimensional periphery of the imperfection. This may be particularly relevant when reviewing crystallographic imperfections that are not in vital positions in the casting. In other words, while castings having imperfections in certain positions may be rendered unfit for use, castings with imperfections in other positions may be acceptable for use, depending on the imperfection size and type. Therefore, creation of the map may facilitate determination of whether a casting having an imperfection is still fit for use.

BRIEF DESCRIPTION OF THE DRAWINGS

Embodiments of the present invention will hereinafter be described in conjunction with the following drawing figures, wherein like numerals denote like elements, and wherein.

DETAILED DESCRIPTION

The following Detailed Description is merely exemplary in nature and is not intended to limit the invention or the application and uses of the invention. Furthermore, there is no intention to be bound by any theory presented in the preceding Background of the Invention or the following Detailed Description.

Figure 1:
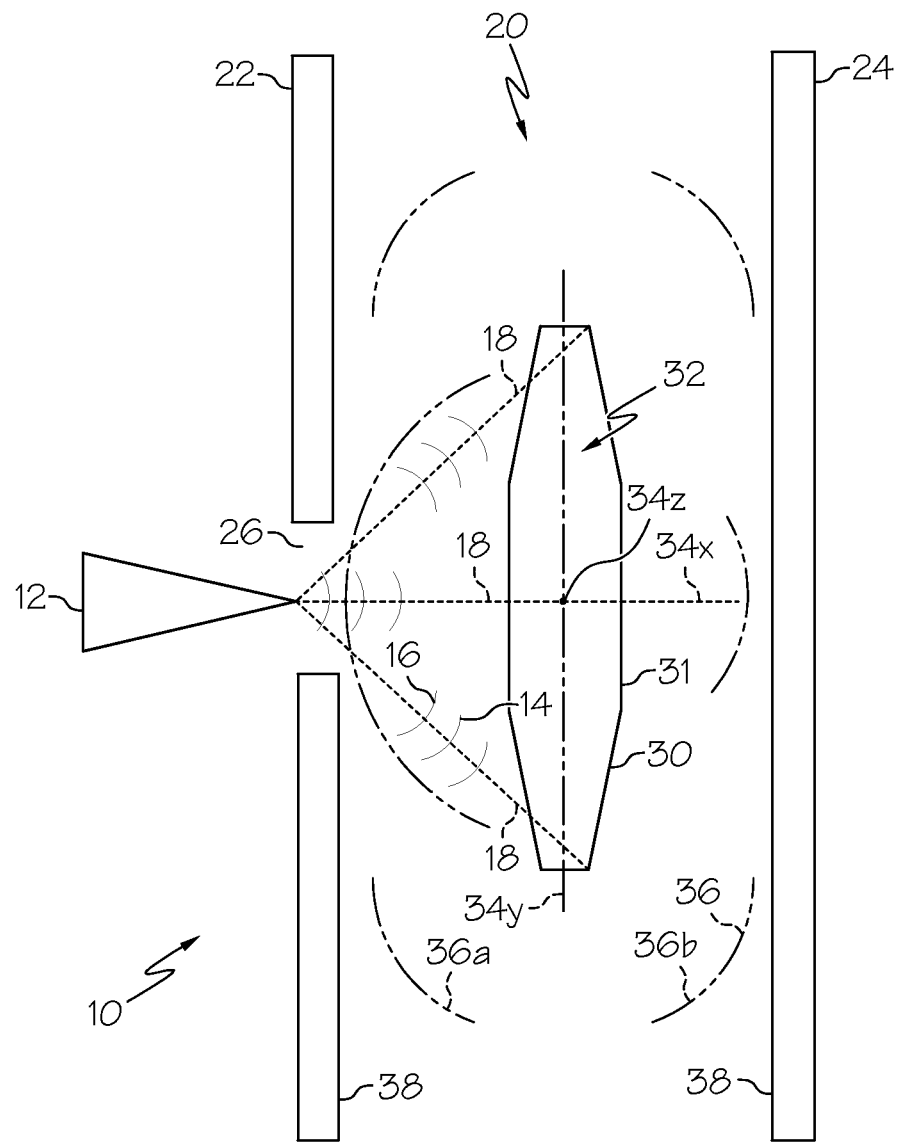
FIG. 1 is a schematic illustration of a system for inspecting a structure for a crystallographic imperfection in accordance with an exemplary embodiment.

Referring to FIG. 1, a system for inspecting structures such as single-crystal superalloy castings in accordance with an exemplary embodiment is shown and generally designated 10. As shown, the system 10 includes an X-ray source 12, such as an X-ray tube, for emitting arrays 14 of X-rays 16 along a plurality of non-parallel paths 18. Further, the system 10 includes a testing area 20 for receiving a structure for inspection. The system 10 further includes capture devices 22, 24 that are positioned before and behind the testing area 20 (relative to the source 12) to allow for digital radiography during inspection as discussed below. As shown, the capture device 22 defines an opening 26 through which the arrays 14 of X-rays 16 pass along their non-parallel paths 18 (three paths are illustrated, though it is understood that arrays 14 of X-rays 16 can be emitted along hundreds of paths).

With the illustrated structures of the system 10 in FIG. 1 defined, the placement of a structure 30, such as a casting, for inspection for a crystallographic imperfection 32 may be discussed. As shown in FIG. 1, the structure 30 is placed in the testing area 20 along the paths 18 at a position 31. Importantly, the position 31 has a measurable location relative to the X-ray source 12 in the direction along the x-axis 34x, the y-axis 34y, and the z-axis 34z. Further, the position 31 includes a measurable orientation of the structure 30 about the x-axis 34x, the y-axis 34y, and the z-axis 34z.

In FIG. 1, X-rays 16 are directed at the structure 30 for diffraction by the crystallographic imperfection 32 to create diffracted X-rays 36. As shown, the diffracted X-rays 36 may include back-reflected X-rays 36a that are reflected back from the structure 30 to be captured by the capture device 22. These back-reflected X-rays 36a may be analyzed to locate an imperfection 32 on the surface of the structure 30. More specifically, an imperfection 32 on the surface of the structure 30 will diffract the oncoming X-rays 16 differently from the rest of the surface of the structure 30. As a result, the back-reflected X-rays 36a will create a two-dimensional pattern 38 on the capture device 22. Graphically, the pattern 38 will include lighter areas including fewer X-ray collisions per area and darker areas with more collisions per area.

Additionally or alternatively, the diffracted X-rays 36 may include transmission X-rays 36b that pass through the structure 30 to be captured by the capture device 24. These transmission X-rays 36b allow for the inspection of subsurface or interior imperfections 32 in the structure 30. Similar to the discussion related to surface imperfections 32, a subsurface imperfection 32 in the interior of the structure 30 will diffract the oncoming X-rays 16 differently from the rest of the internal volume of the structure 30. As a result, the transmission X-rays 36b will create a two-dimensional pattern 38 on the capture device 24. Again, the pattern 38 will include lighter areas including fewer X-ray collisions per area and darker areas with more collisions per area.

For purposes of the present embodiment, a plurality of patterns 38 are captured and compared with one another or otherwise analyzed to locate crystallographic imperfections 32 in the structure 30. Specifically, a pattern 38 is captured for each of a sequence of different positions 31 of the structure 30 relative to the X-ray source 12. The position 31 of the structure 30 is directly related to the resulting pattern 38, and the positional data is used in the comparison of patterns 38 to locate the imperfections 32 as is understood in radiography.

Figure 2:
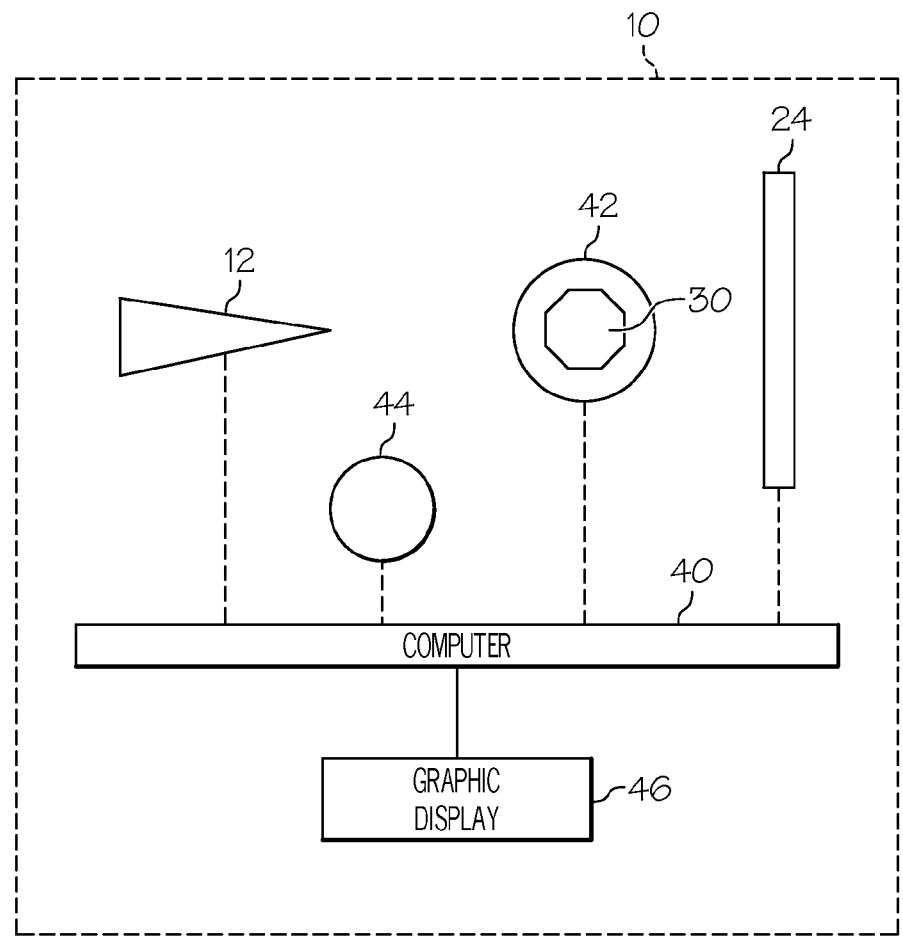
FIG. 2 is a schematic illustration of the system of FIG. 1 shown in communication with a computer for automated operation of the system in accordance with an exemplary embodiment.

Referring to FIG. 2, the system 10 is shown to provide for automatic operation and analysis to locate imperfections 32. In FIG. 2, the X-ray source 12 and capture devices 22, 24 are connected to a computer 40. Also, the structure 30 is shown to be situated on a mount 42 that is connected to the computer 40. Further, the computer 40 is in communication with a marking device 44 and a display device 46.

As may be understood by cross-referencing FIGS. 1 and 2, the computer 40 is able to place the structure 30 at an initial position 31 and activate the X-ray source 12 to direct X-rays 16 at the structure 30 for a selected exposure time. After the X-rays 16 are diffracted and the diffracted X-rays 36 are captured by the capture device 22, 24, the pattern 38 of diffracted rays 36 is communicated to the computer 40 by the capture device 22, 24. The computer 40 then moves the structure 30 to a new position 31 and repeats the X-ray procedure. The computer 40 may move the structure 30 to a sequence of scripted positions or to a sequence of positions determined based on ongoing analysis of the already-received patterns 38. Because the profile of the X-rays is enhanced and the process is automated, numerous patterns 38 may be captured in a short amount of time.

Upon location of a crystallographic imperfection 32, the computer 40 may instruct the marking device 44 to mark the imperfection 32 with a target of paint, ink, resin or the like, or the computer 40 may create a three dimensional map of the structure 30 and the location of the imperfection 32 for graphic display, either electronically on the display device 46 a monitor or printed via a non-illustrated printer.

Figure 3:
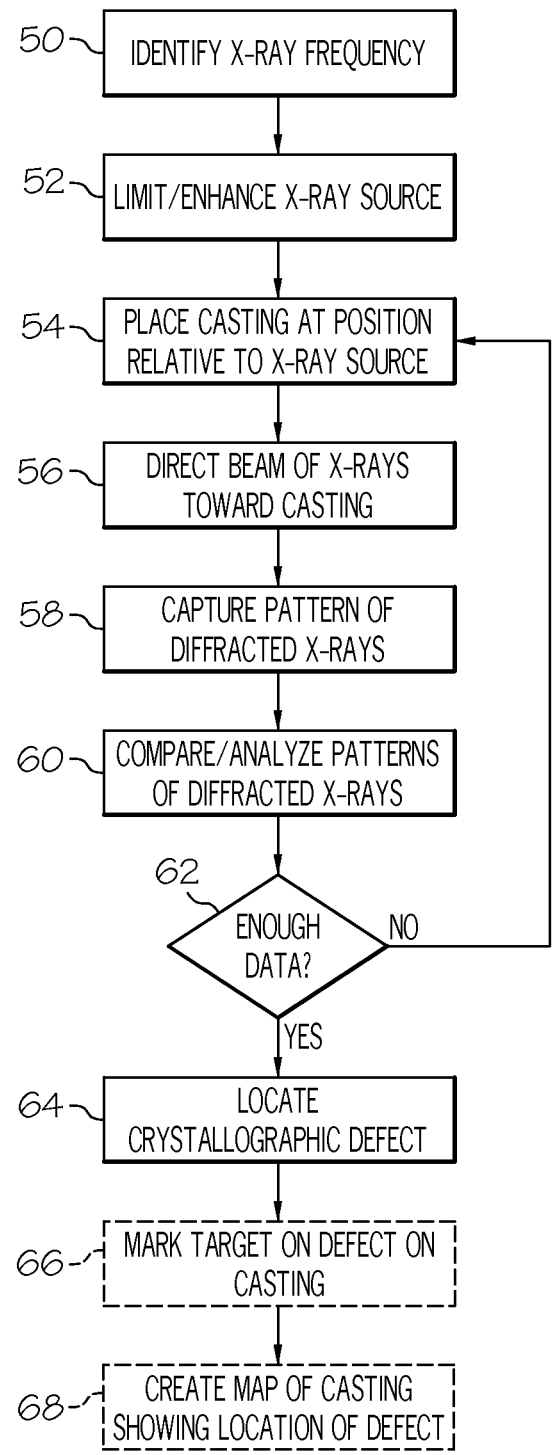
FIG. 3 is a flow chart representing the method of inspecting a structure for a crystallographic imperfection in accordance with an exemplary embodiment.

Referring now to FIG. 3, the method of an embodiment is illustrated in a flow chart. Initially, an X-ray wavelength susceptible to diffraction by a crystallographic imperfection is identified at 50. As stated above, the wavelength may include a single monochromatic X-ray, a band of wavelengths, or a plurality of noncontiguous wavelengths.

After the wavelength is identified, the X-ray source 12 is limited and/or enhanced at 52 to emit arrays 14 having a high fraction of X-rays 16 of the identified wavelength, such as over fifty percent, to produce useable diffraction imaging with a short exposure time. This is done so as to maximize diffraction by any crystallographic imperfection that may be present. By maximizing diffraction, the patterns 38 of diffracted X-rays 36 are amplified so that small imperfections are more easily located. The output of the X-ray source 12 may be enhanced by changing the X-ray tube target material, changing the X-ray tube voltage, filtering to remove non-interactive X-ray wavelengths, or through other methods including the use of synchrotrons. Enhancement of the array 14 of X-rays 16 will result in a shortening of the amount of time needed for capturing a proper pattern 38 of diffracted X-rays 36 as well as improved sharpness of the pattern 38.

At 54, the structure 30 is placed at a position 31 relative to the X-ray source 12. Thereafter, the array 14 of X-rays 16 is directed toward the structure 30 along non-parallel paths 18 at 56 for diffraction by an imperfection 32 at 56. At 58, the diffracted X-rays 36 are captured by the capture device 22, 24 and the pattern 38 of diffracted X-rays 36 is communicated to the computer 50.

The computer 50 compares or otherwise analyzes the patterns 38 at 60, and determines whether more data (e.g., additional patterns 38) is needed at inquiry 62. If more data is needed, then the computer 50 moves the structure 30 to a new position 31 at 54 and repeats the succeeding steps until the inquiry 62. When more data is not necessary, the location of the crystallographic imperfection 32 is performed at 64 by comparing patterns 38. Specifically, pattern elements such as the presence and position of lighter areas (indicating fewer X-ray collisions) and darker areas (indicating more X-ray collisions) are analyzed in each pattern 38 in view of the associated casting position 31. A comparison of these pattern elements for a plurality of patterns 38 indicates what pattern elements are caused by a crystallographic imperfection 32, and the location and physical characteristics of that crystallographic imperfection 32. After the location of the crystallographic imperfection 32 is performed, the marking device 44 may mark a target on the imperfection 32 or the structure 30 at 66 and/or create a map of the structure 30 showing the location of the imperfection 32 at 68.

Figure 4:
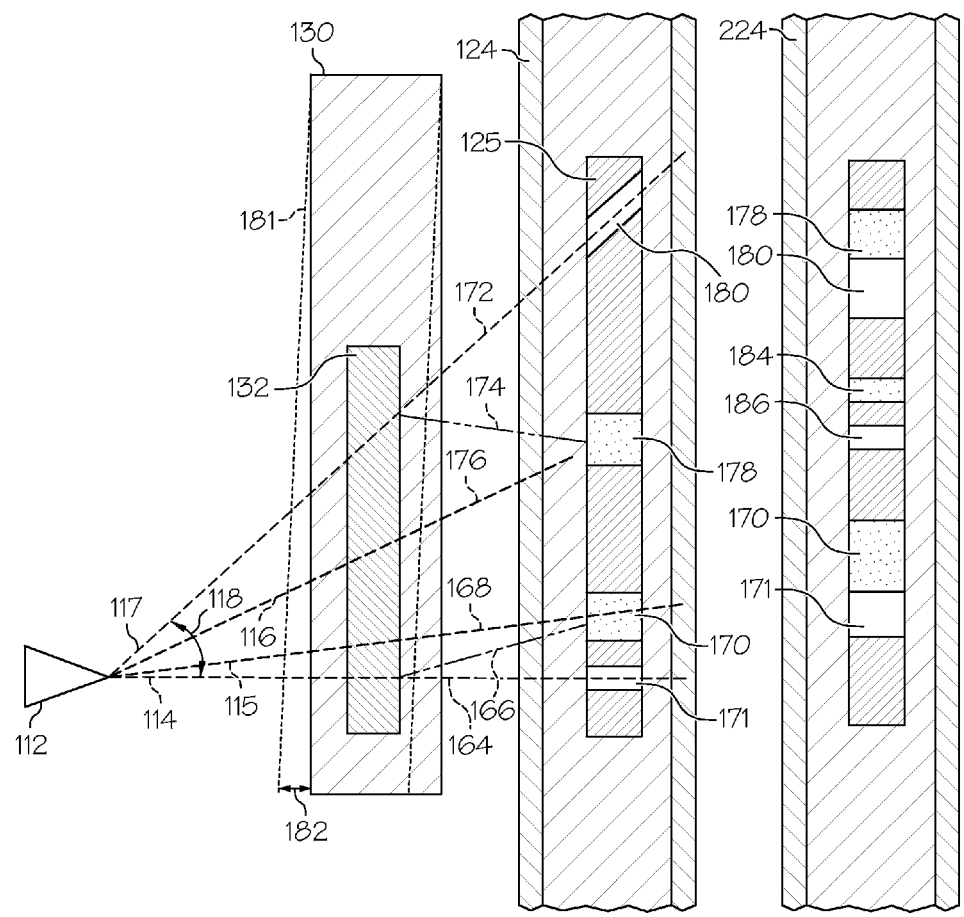
FIG. 4 is a schematic illustration depicting the results of an inspection of a structure for a crystallographic imperfection in accordance with an exemplary embodiment.

Referring now to FIG. 4, exemplary results of an inspection are illustrated. As shown, an X-ray source 112 is configured to emit non-parallel beams such as exemplary beams 114, 115, 116, and 117. Beams 115, 116 and 117 are separated from perpendicular beam 114 by a divergence angle, for example the divergence angle between beams 114 and 117 identified by arrow 118. Further, each beam 114, 115, 116, and 117 is directed at a casting 130 which contains a crystallographic imperfection 132. In FIG. 4, the beams are shown passing through the casting 130, and the resulting film 124 produced by a capture device positioned beyond the casting 130, although such beams may be reflected back to capture device position between the casting 130 and the source 112. In FIG. 4, the X-ray source 112 and casting 130 are presented in cross-section view, while the resulting film 124 is illustrated as a top view. Further, while the film 124 includes cross hatching for clarity, in actuality, shading typical of an X-ray capture would be present.

As shown in FIG. 4, beam 114 is diffracted from its path 164 to a diffracted path 166 which reaches the capture device 124. Further, beam 115 reaches the capture device 124 along a substantially non-diffracted or slightly diffracted path 168. As paths 166 and 168 intersect the capture device as substantially the same position, the film 124 registers a dark area in a section 125 indicative of the crystallographic imperfection 132. Further, as beam 114 is diffracted off of path 164, the film 125 registers a light area 171 at its intersection with path 164.

This occurrence is repeated with beams 116 and 117. As shown, beam 117 is diffracted from path 172 to path 174. Further, beam 116 is substantially non-diffracted or slightly diffracted and remains on path 176. As paths 174 and 176 strike the film 124 at substantially the same position, a dark area 178 is registered by the capture device 124. Further, as beam 117 is diffracted from its path 172, a light area 180 is registered at the intersection of path 172 and the film 124.

The existence and position of the dark areas 170 and light area 171 are caused by wavelength induced diffraction. Where more X-rays reach the film 124, darker areas are created, and where fewer X-rays reach the film 124, lighter areas are registered. This is repeated with dark area 178 and light area 180. Further, dark area 178 and light area 180 also exhibit divergence angle induced diffraction, as beams 116 and 117 were emitted at divergence angles from the perpendicular beam 114.

In FIG. 4, it can be seen that the casting 130 may be pivoted to a new position indicated by dotted line 181 which is at a tilt angle of few degrees or more and represented by arrow 182. As a result of tilting the casting 130, the resulting pattern of dark and light areas is changed. The film produced by the capture device is shown with the changed pattern as indicated by numeral 224. As shown, dark and light areas 170, 171, 178, 180 are moved as a result of tilting the casting 130. Further, additional dark areas 184 and light areas 186 may be created, as a result of random satisfaction of Bragg angle and wavelength conditions.

As can be seen from FIG. 4, a combination of wavelength, divergence angle, and tilt angle (which may be three-dimensional) allows for the analysis of patterns of dark and light areas that indicate the impact or absence of X-ray beams. The analysis results in the identification of crystallographic imperfections as well as their location and boundaries.

While at least one exemplary embodiment has been presented in the foregoing Detailed Description, it should be appreciated that a vast number of variations exist. It should also be appreciated that the exemplary embodiment or exemplary embodiments are only examples, and are not intended to limit the scope, applicability, or configuration of the invention in any way. Rather, the foregoing Detailed Description will provide those skilled in the art with a convenient road map for implementing an exemplary embodiment of the invention, it being understood that various changes may be made in the function and arrangement of elements described in an exemplary embodiment without departing from the scope of the invention as set forth in the appended Claims and their legal equivalents.

What is claimed is:

1. A method of inspecting a structure comprising:
   configuring an X-ray source to emit X-rays of a predetermined X-ray wavelength;
   placing the structure at a plurality of positions relative to the X-ray source;
   for each of the positions, directing non-parallel arrays of X-rays of the predetermined X-ray wavelength at the structure for diffraction by a crystallographic imperfection to create a pattern of diffracted X-rays;
   capturing each pattern of diffracted X-rays; and
   comparing each of the captured patterns of diffracted X-rays to one another to locate the crystallographic imperfection.

2. The method of claim 1 wherein each array of X-rays comprises monochromatic X-rays.

3. The method of claim 1 further comprising:
   marking the detected crystallographic imperfection with a target for physical removal of the crystallographic imperfection.

4. The method of claim 1 further comprising:
   creating a map of the structure to communicate a location of the crystallographic imperfection.

5. The method of claim 4 wherein the map discloses a three-dimensional periphery of the crystallographic imperfection.

6. The method of claim 1 wherein the diffracted X-rays pass through the structure.

7. The method of claim 1 wherein the patterns of diffracted X-rays are captured by a digital image capture device.

8. The method of claim 7 wherein the digital image capture device communicates the captured patterns of diffracted X-rays to a computer, and wherein the computer determines subsequent positions in view of the communicated captured patterns of diffracted X-rays.

9. The method of claim 8 wherein the computer places the structure at the plurality of positions relative to the X-ray source.

10. The method of claim 1 further comprising:
    enhancing the X-ray source to emit a selected profile of X-rays in the identified X-ray wavelength.

11. The method of claim 1 wherein the structure has a surface, wherein the crystallographic imperfection is on the surface, and wherein the diffracted X-rays are reflected off of the surface in a backward direction to create each pattern of diffracted X-rays.

12. A method of inspecting an unetched single-crystal superalloy casting for a crystallographic imperfection with an ascertainable diffractive affect on X-rays in an identified X-ray wavelength, the method comprising:
    placing the casting at a plurality of sequential positions relative to an X-ray source;
    for each of the sequential positions, directing non-parallel arrays of X-rays in the identified X-ray wavelength from the X-ray source toward the casting for diffraction by the crystallographic imperfection to create a pattern of diffracted X-rays;
    capturing each sequential pattern of diffracted X-rays; and
    analyzing the sequential patterns of diffracted X-rays to locate the crystallographic imperfection.

13. The method of claim 12 further comprising:
    marking the detected crystallographic imperfection with a target for physical removal of the crystallographic imperfection.

14. The method of claim 13 wherein the X-ray source is limited to only direct X-rays in the identified X-ray wavelength toward the casting to maximize diffraction by the crystallographic imperfection.

15. The method of claim 14 wherein the casting has an interior, wherein the diffracted X-rays pass through the casting, and wherein the crystallographic imperfection is in the interior of the casting.

16. The method of claim 15 wherein the sequential patterns of diffracted X-rays are captured by a digital image capture device.

17. The method of claim 16 wherein the digital image capture device communicates the sequential patterns of diffracted X-rays to a computer, and wherein the computer determines subsequent sequential positions in view of the communicated sequential patterns of diffracted X-rays.

18. The method of claim 17 wherein the computer places the casting at the plurality of sequential positions relative to the X-ray source.

19. The method of claim 18 further comprising:
enhancing the X-ray source to emit a selected profile of X-rays in the identified X-ray wavelength.

20. A system for inspecting an unetched structure comprising:
an X-ray source configured to direct X-rays toward the structure;
a capture device configured to capture a pattern of X-rays diffracted by an imperfection in the structure;
a structure mount configured to have the structure mounted thereon, the structure mount further configured to be controllably moved, to thereby move the structure to a plurality of positions; and
a processor in operable communication with the X-ray source, the structure mount, and the capture device, the processor configured to control the X-ray source to emit X-rays of a predetermined wavelength, the processor configured to controllably position the structure mount at the plurality of positions, and the processor further configured to compare the captured patterns of diffracted X-rays to locate a crystallographic imperfection.

* * * * *